US007501126B2

(12) United States Patent
Roizman et al.

(10) Patent No.: US 7,501,126 B2
(45) Date of Patent: Mar. 10, 2009

(54) TARGETING OF HERPES SIMPLEX VIRUS TO SPECIFIC RECEPTORS

(75) Inventors: Bernard Roizman, Chicago, IL (US); Gouying Zhou, Chicago, IL (US); Guo J. Ye, San Diego, CA (US)

(73) Assignee: The University of Chicago, Chicago, IL (US)

( * ) Notice: Subject to any disclaimer, the term of this patent is extended or adjusted under 35 U.S.C. 154(b) by 365 days.

(21) Appl. No.: 10/530,774

(22) PCT Filed: Oct. 6, 2003

(86) PCT No.: PCT/US03/31598

§ 371 (c)(1), (2), (4) Date: Nov. 17, 2005

(87) PCT Pub. No.: WO2004/033639

PCT Pub. Date: Apr. 22, 2004

(65) Prior Publication Data

US 2006/0068391 A1 Mar. 30, 2006

Related U.S. Application Data

(60) Provisional application No. 60/416,716, filed on Oct. 7, 2002.

(51) Int. Cl.
*A01N 63/00* (2006.01)
*A61K 39/245* (2006.01)

(52) U.S. Cl. ................ 424/199.1; 424/93.2; 424/231.1; 435/235.1

(58) Field of Classification Search ....................... None
See application file for complete search history.

(56) References Cited

U.S. PATENT DOCUMENTS

| | | | |
|---|---|---|---|
| 5,328,688 | A | 7/1994 | Roizman |
| 5,599,691 | A | 2/1997 | Roizman |
| 2005/0271620 | A1 | 12/2005 | Brown et al. |

FOREIGN PATENT DOCUMENTS

| | | | |
|---|---|---|---|
| WO | WO 99/06583 | * | 2/1999 |

OTHER PUBLICATIONS

Debinski et al (Clinical Cancer Research 5: 985-990, 1999) (cited in IDS).*
van Beusechem et al (Journal of Virology 76:2753-2762, Mar. 2002).*
Laquerre et al (Journal of Virology 72:9683-9697, 1998).*
Spear, P.G. Cellular Microbiology 6(5): 401-410 (2004).*
Garner, J.A. Advanced Drug Delivery Reviews 55: 1497-1513 (2003).*
Arsenakis, et al., "Expression and Regulation of Glycoprotein C Gene of Herpes Simplex Virus 1 Resident in a Clonal L-Cell Line," J. Virol. 58(2):367-76 (1986).
Brooks, et al., "Ingerin $\alpha_v\beta_3$ Antagonists Promote Tumor Regression by Inducing Apoptosis of Angiogenic Blood Vessels," Cell 79:1157-1164 (1994).
Brooks, et al., "Requirement of Vascular Integrin $\alpha_v\beta_3$ for Angiogenesis," Science 264:569-571 (1994).
Brunetti, et al., "Herpex Simplex Virus gD and Virions Accumulate in Endosomes by Mannose 6-Phosphate-Dependent and -Independent Mechanisms," J of Virol 72(4):3330-3339 (1998).
Burger, et al., "Expression Analysis of δ-Catenin and Prostate-Specific Membrane Antigen: Their Potential as Diagnostic Markers for Prostate Cancer," Int. J. Cancer 100:228-237 (2002).
Campadelli-Flume, et al., "The novel receptors that mediate the entry of herpes simplex viruses and animal alphaherpesviruses into cells," Rev. Med. Virol. 10:305-319 (2000).
Carfi, et al., "Herpes Simplex Virus Glycoprotein D Bound to the Human Receptor HveA," Mol. Cell. 8(1):169-79 (2001).
Cassady, et al., "The Second-Site Mutation in the Herpex Simplex Virus Recombinants Lacking the $\gamma_1$ 34.5 Genes Precludes Shutoff of Protein Synthesis by Blocking the Phosphorylation of eIF-2α" J. Virol. 72(9):7005-11 (1998).
Chou, et al., "Association of a $M_r$ 90,000 phosphoprotein with protein kinase PKR in cells exhibiting enhanced phosphorylation of translation initiation factor eIF-2α and premature shutoff of protein synthesis after infection with $\gamma_1 34.5^-$ mutants of herpes simplex virus 1," Proc Natl Acad Sci USA 92(23):10516-20 (1995).
Cocchi, et al., "The Ectodomain of a Novel Member of the Immunoglobulin Subfamily Related to the Poliovirus Receptor Has the Attributes of a Bona Fide Receptor for Herpes Simplex Virus Types 1 and 2 in Human Cells," J. Virol. 72:9992-10002 (1998).
Connolly, "Potential Nectin-1 Binding Site on Herpes Simplex Virus Glycoprotein D," *J. Virol*, 79: 1282-1295 (2005).
Davis, et al., "Survival rates in patients with primary malignant brain tumors stratified by patient age and tumor histological type: an analysis based on Survellance, Epidemiology, and End Results (SEER) data, 1973-1991" J. Neurosurg. 88:1-10 (1998).
Debinski, "An Immune Regulatory Cytokine Receptor and Glioblastoma Multiforme: An Unexpected Link," Crit. Rev. Oncogen 9:255-268 (1998).
Ross, et al., "Prostate Stem Cell Antigen as Therapy Target: Tissue Expression and in Vivo Efficacy of an Immunoconjugate," Cancer Res. 62:2546-2553 (2002).
Ruoslahti, E., "RGD and Other Recognition Sequences for Integrins," Annu. Rev. Cell Dev. Biol. 12:697-715 (1996).
Rux et al., "Functional Region IV of Glycoprotein D from Herpes Simplex Virus Modulates Glycoprotein Binding to the Herpesvirus Entry Mediator," Journal of Virology, 72(9):7091-7098 (1998).

(Continued)

*Primary Examiner*—Mary E Mosher
(74) *Attorney, Agent, or Firm*—Marshall, Gerstein & Borun LLP

(57) ABSTRACT

The invention relates to engineered Herpes simplex virus (HSV) particles that are targeted to one or more specific receptors. Also, recombinant vectors for producing such HSV particles. By reducing the affinity of HSV for its natural receptor(s) and increasing the affinity for a selected receptor, the HSV particles of the invention may be used for targeting cells that express the selected receptor. The ability to selectively target cells renders the HSV particles particularly useful in selectively killing the selected receptor-bearing cells (such as tumor cells), imaging cells bearing the selected receptor, and providing gene replacement therapy to cells bearing the selected receptor.

13 Claims, 6 Drawing Sheets

OTHER PUBLICATIONS

Sharma, et al., "Molecular Imaging of Gene Expression and Protein Function In Vivo With PET and SPECT," J Magn Reson Imaging 16(4):336-51 (2002).

Simard, et al., "Sequence Analysis of the UL39, UL38, and UL37 Homologues of Bovine Herpesvirus 1 and Expression Studies of UL40 and UL39, the Subunits of Ribonucleotide Reductase," Virology 212(2):734-40 (1995).

Soling, et al., "Intracellular localization of Herpes simplex virus type 1 thymidine kinase fused to different fluorescent proteins depends on choice of fluorescent tag," FEBS Lett. 527(1-3):153 (2002).

Spear, et al., "Three Classes of Cell Surface Receptors for Alphaherpesvirus Entry," Virology 275:1-8 (2000).

Thomas, et al., "Preoperative Combined Nested Reverse Transcriptase Polymerase Chain Reaction for Prostate-Specific Antigen and Prostate-specific Membrane Antigen Does Not Correlate With Pathologic Stage or Biochemical Failure in Patients With Localized Prostate Cancer Undergoing Radical Prostatectomy," J. Clin. Oncol. 20:3213-3218 (2002).

Turner, et al., "Glycoproteins gB, gD, and gHgL of Herpes Simplex Virus Type 1 Are Necessary and Sufficient to Mediate Membrane Fusion in a Cos Cell Transfection System," J of Virol 72(1): 873-75 (1998).

Urbanelli, et al., "Targeted Gene Transduction of Mammalian Cells Expressing the HER2/neu Receptor by Filamentous Phage," J Mol Biol. 313(5):965-76 (Nov. 9, 2001).

Ye, et al., "The essential protein encoded by the $U_L31$ gene of herpes simplex virus 1 depends for its stability on the presence of $U_L34$ protein," Proc. Natl. Acad. Sci. USA 97(20):11002-7 (2000).

Zago et al., "Use of herpes simplex virus and pseudorabies virus chimeric glycoprotein D molecules to identify regions critical for membrane fusion," *Proc. Natl. Acad. Sci. USA*., 101: 17498-17503 (2004).

Zhou et al., "Characterization of a Recombinant Herpes Simplex Virus 1 Designed to Enter Cells via the IL13Rα2 Receptor of Malignant Glioma Cells," *J. Virol*, 9: 5272-5277 (2005).

Zhou, et al., "Glycoprotein D or J Delivered in *trans* Blocks Apoptosis in SK-N-SH Cells Induced by a Herpes Simplex Virus 1 Mutant Lacking Intact Genes Expressing Both Glycoproteins," J. Virol, 74(24):11782-91 (2000).

Zhou, et al., "The Domains of Glycoprotein D Required to Block Apoptosis Depend on Whether Glycoprotein D is Present in the Virions Carrying Herpes Simplex Virus 1 Genome Lacking the Gene Encoding the Glycoprotein," J. Virol. 75(13):6166-72 (2001).

Zhou, et al., "Cation-Independent Mannose 6-Phosphate Receptor Blocks Apoptosis Induced by Herpes Simplex Virus 1 Mutants Lacking Glycoprotein D and Is Likely the Target of Antiapoptotic Activity of the Glycoprotein," J. Virol. 76(12):6197-204 (2002).

Debinski, et al., "Receptor for Interleukin 13 Is a Marker and Therapeutic Target for Human High-Grade Gliomas[1]," Clin. Cancer Res. 5:985-990 (1999).

Debinski, et al., "Retargeting Interleukin 13 for Radioimmunodetection and Radioimmunotherapy of Human High-grade Gliomas," Clin. Cancer Res. 5(10 Suppl):3143s-3147s (1999).

Debinski, et al., "Molecular Expression Analysis of Restrictive Receptor for Interleukin 13, a Brain Tumor-associated Cancer/Testis Antigen," Mol. Med. 6:440-449 (2000).

de Vires et al., "Scintrigraphic Imaging of HSVtk Gene Therapy," Current Pharmaceutical Design 8:1435-1450 (2002).

de Vries, et al., "Positron emission tomography: measurement of transgene expression," Methods 27(3) :234-241 (2002).

Ellerman, et al., "Identification of a Determinant of Epidermal Growth Factor Receptor Ligand-Binding Specificity Using a Tuncated, High-Affinity Form of the Ectodomain," Biochemistry 40:8930-8939 (2001).

Fracasso, et al., "Anti-tumor Effects of Toxins Targeted to the Prostate Specific Membrane Antigen," Prostate 53:9-23 (2002).

Gembitsky, et al., "A specific binding site for a fragment of the B-loop of epidermal growth factor and related peptides," Peptides 23:97-102 A. (2001).

Hayashi, et al., "MUC1 Mucin Core Protein Binds to the Domain 1 of ICAM-1," Digestion 63:87-92 (2001).

He, et al., "Suppression of the Phenotype of $\gamma_1$ 34.5⁻ Herpes Simplex Virus 1: Failure of Activated RNA-Dependent Protein Kinase to Shut Off Protein Synthesis is Associated with a Deletion in the Domain of the α47 Gene," J. Virol. 71(8):6049-54 (1997).

International Search Report from PCT/US03/31598 (2004).

Laquerre, et al., "Heparan Sulfate Proteoglycan Binding by Herpes Simplex virus Type 1 Glycoproteins B and C, Which Differ in Their Contributions to Virus Attachment, Penetration, and Cell-to-Cell Spread," J. Virol. 72(7):6119-30 (1998).

Leib, et al., "Interferons Regulate the Phenotype of Wild-type and Mutant Herpes Simplex Viruses In Vivo," J. Exp. Med. 189:663-672 (1999).

Lorimer, et al., "Targeting retrovirus to cancer cells expressing a mutant EGF receptor by insertion of a single chain antibody variable domain in the envelope glycoprotein receptor binding lobe," J Immunol Methods 237(1-2):147-57 (2000).

Mabjeesh, et al., "Gene therapy of prostate cancer: current and future directions," Endo. Related Cancer 9:115-139 (2002).

Manoj et al., "Mutations in herpes simplex virus glycoprotein D that prevent cell entry via mectins and alter cell tropism," *Proc. Natl. Acad. Sci. USA*., 101: 12414-12421 (2004).

Markert, et al., "Conditionally replicating herpes simplex virus mutant, G207 for the treatment of malignant glioma: results of a phase I trial," Gene Ther. 7(10):867-74 (2000).

McKie, et al., "Histopathological responses in the CNS following inoculation with a non-neurovirulent mutant (1716) of herpes simplex virus type 1 (HSV 1): relevant for gene and cancer therapy," Neuropathol Appl Neurobiol. 24(5):367-72 (1998).

Mineta, et al., "Attenuated multi-mutated herpes simplex virus-1 for the treatment of malignant gliomas," Nat Med., 1(9):938-43 (1995).

Mintz A., et al., "Il-13Rα2 is a Glioma-Restricted Receptor for Interleukin-13," Neoplasia 4:388-399 (2002).

Montgomery, et al., "Herpes Simplex Virus-1 Entry into Cells Mediated by a Novel Member of the TNF/NGF Receptor Family," Cell 87:427-436 (1996).

Pyles, et al., "A Novel Multiply-Mutated HSV-1 Strain for the Treatment of Human Brain Tumors," Human Gene Ther. 8(5):533-44 (1997).

Rampling, et al., "Toxicity evaluation of replication-competent herpes simplex virus (ICP 34.5 null mutant 1716) in patients with recurrent malignant glioma," Gene Ther. 7(10):859-66 (2000).

* cited by examiner

A. The amino terminal sequence of IL13-gC gcttggtcgggaggccgcatcgaacgcacacccccatccggtggtccgtgtggaggtcgttttcagtgcc
cggtctcgctttgccgggaacgctagcctcATGGCGCTTTTGTTGACCACGGTCATTGCTCTCACTTGCCt
gC upstream ← IL-13*
TGGCGGCTTTGCCTCCCCAGGCCCTGTGCCTCCCTCTACAGCCCTCAGGTACCTCATTGAGGAGCTGGTCA
ACATCACCCAGAACCAGAAGGCTCCGCTCTGCAATGGCAGCATGGTATGGAGCATCAACCTGACAGCTGGC
ATGTACTGTGCAGCCCTGGAATCCCTGATCAACGTGTCAGGCTGCAGTGCCATCGAGAAGACCCAGAGGAT
GCTGAGCGGATTCTGCCCGCACAAGGTCTCAGCTGGGCAGTTTTCCAGCTTGCATGTCCGAGACACCAAAA
TCGAGGTGGCCCAGTTTGTAAAAGATCTGCTCTTACATTTAAAGAAACTTTTTCGCGAGGGACGGTTgaat
tcCACCCGCATGGAGTTCCGCCTCCAGATATGGCGTTACTCCATGGGTCCGTCCCCCCCAATCGCTCCGGC
→ gC downstream

B. The sequence of the $gB_{\Delta poly(K)}$ domain

GGGTCCTGGTGGCGTCGGCGGCTCCGAGTTCCCCCGGCACGCCTGGGGTCGCGGCCGCGACCCAGGCGGC
GAACGGGGGACCTGCCACTCCGGCGCCGCCCGCCCCTGGCCCCGCCCCAACGGGGGATCCGAAACCGAAG
AAGAACAGAAAACCGAAACCCCCAAAGCGCCGCGCCCCGCCGGCGACAACGCGACCGTCGCCGCGGGCCA
CGCCACCCTGCGCGAGCACCTGCGGGACATCAAGGCGGAGAACACCGATGCAAACTTTTACGTGTGCCCA
CCCCCCACGGGCGCCACGGTGGTGCAGTTCGAGCAGCCGCGCCGCTGCCCGACCCGGCCCGAGGGTCAGA

C. The amino terminal sequence of IL13-gD

ATGGGGGGGGCTGCCGCCAGGTTGGGGGCCGTGATTTTGTTTGTCGTCATAGTCGGCCTC
Signal peptide of gD→
CATGGGGTCCGCGGCAAATATGCCTTGGCGGATGCCTCTCTCAAGCTGGCCGACCCCAAT
←
CGCTTTCGCCGCAAAGACCTTCCGGTCctcgag*ATGGCGCTTTTGTTGACCACGGTCATT
24AA XhoI IL13→
GCTCTCACTTGCCTTGGCGGCTTTGCCTCCCCAGGCCCTGTGCCTCCCTCTACAGCCCTC
AGGGAGCTCATTGAGGAGCTGGTCAACATCACCCAGAACCAGAAGGCTCCGCTCTGCAAT
GGCAGCATGGTTTGGAGCATCAACCTGACAGCTGGCATGTACTGTGCAGCCCTGGAATCC
CTGATCAACGTGTCAGGCTGCAGTGCCATCGAGAAGACCCAGAGGATGCTGGGCGGATTC
TGCCCGCACAAGGTCTCAGCTGGGCAGTTTTCCAGCTTGCATGTCCGAGACACCAAAATC
GAGGTGGCCCAGTTTGTAAAGGACCTGCTCTTACATTTAAAGAAACTTTTTCGCGAGGGA
CGGTTCAACTGAAAC*ggtaccCTGGACCAGCTGACCGACCCTCCGGGGGTCCGGCGCGTG
←IL13 KpnI 25AA
TACCACATCCAGGCGGGCCTACCGGACCCGTTCCAGCCCCCCAGCCTCCCGATC

FIGURE 2 pgD- in pcDNA3.1(-) with CMV promoter collapsed by NruI/NheI digestion. The fragment containing gD upstream at NotI/BamHI, and gD downstream at XhoI/KpnI in pBluescript II SK was excised by NotI/KpnIand ligated into pcDNA3.1(-) in which the CMV promoter had been collapsed. N, NotI, B, BamHI, P, PstI, E, EcoRI, H, HindIII, C, ClaI, X, XhoI, and K, KpnI.

TARGETING OF HERPES SIMPLEX VIRUS TO SPECIFIC RECEPTORS

GOVERNMENT INTERESTS

The U.S. Government owns rights in the invention pursuant to National Cancer Institute grant number 1PO1 CA71933.

BACKGROUND OF THE INVENTION

A steady rate of healthcare advances has led to continuing improvement in the health and quality of life for humans and animals. Nevertheless, a variety of diseases, disorders, and conditions have largely eluded the best efforts at prevention or treatment. Chief among these maladies is the loss of cell-cycle control that frequently results in the undesirable cell proliferation characteristic of cancer in its many forms, such as malignant glioma. Malignant gliomas are devastating brain tumors that afflict animals such as humans. The average life span after diagnosis is less than one year and few patients have been reported to survive five years. Furthermore, none of the conventional anti-cancer therapies has been successful in significantly prolonging the lifespan of patients with this disease. In recent years there have been numerous attempts to use genetically engineered herpes simplex viruses (HSV) as oncolytic agents to treat malignant gliomas. Because wild-type viruses are highly virulent, the viruses used in preclinical evaluations and in phase-1 clinical studies have been thoroughly attenuated. While several deletion mutants have been tested, the mutants that reached clinical trials lacked the $\gamma_1$34.5 gene encoding infected cell protein 34.5 (ICP34.5) and optionally, the $U_L$39 gene encoding the large subunit of ribonucleotide reductase.

These attenuated HSV viruses, however, have been imperfectly engineered as oncolytic agents. One advantage of these mutant viruses is that they have a significantly reduced capacity to replicate in normal, non-dividing cells in vivo. Viral ribonucleotide reductase is an essential gene for viral replication in resting cells and, hence, the $U_L$39 mutant virus is dysfunctional in the normal environment of the central nervous system (Simard et al. 1995). The major function of ICP34.5 is to preclude the shutoff of protein synthesis caused by activation of protein kinase R in infected cells. Once activated, this enzyme phosphorylates the $\alpha$ subunit of translation initiation factor 2 (eIF2$\alpha$), resulting in complete cessation of translation. Mutants lacking the $\gamma_1$34.5 genes are highly attenuated because the lytic life cycle is completely blocked in an interferon$^+$ cellular background. In contrast, $\gamma_1$34.5 mutants are nearly as virulent as wild-type virus in mice lacking interferon receptor. Although mutants deleted in both $\gamma_1$34.5 and $U_L$39 are not significantly more attenuated than those lacking the $\gamma_1$34.5 genes, such mutants do provide added insurance in the form of a reduced risk of reversion.

A significant disadvantage of these mutant HSV viruses is their poor replication, even in dividing cells. In experimental animal systems, the mutant viruses do not exhibit sustained lytic life cycles, with the loss of a potentially amplified response to a given therapeutic dose of the virus that would be expected upon re-infection of tumor cells by the multiplied viral progeny. Consequently, maximum killing of tumors cells requires high doses of virus. Given the poor growth of these mutant HSV viruses, even in dividing cells, production of virus pools large enough to yield efficacious inocula of>$10^9$ plaque forming units (PFU) has remained a major obstacle. Moreover, indiscriminate binding of virus to non-tumor cells further diminishes the effectiveness of HSV virus dosages because mis-targeted viral particles do not contribute to the desired beneficial therapeutic effect of tumor cell destruction. One approach to overcoming these obstacles is to achieve a more thorough understanding of the HSV lytic life cycle and thereby facilitate the development of HSV mutants tailored for use as targeted therapeutic agents, such as targeted oncolytic agents.

HSV enters host cells using a two-step mechanism. The first step of entry is HSV attachment to the cell surface. This step is initiated by glycoproteins B and C (gB and gC), which project from the viral envelope, attaching to heparan sulfate proteoglycans on host cell surfaces. The gB and gC domains interacting with heparan sulfate have been mapped at the sequence level (Laquerre et al. 1998). Following this initial attachment, viral glycoprotein D (gD) interacts with one of several receptors. Of these gD receptors, two are particularly important for entry (Spear et al, 2000). One receptor, designated HveA, is a member of the family of receptors for tumor necrosis proteins. A second receptor, designated HveC, is a member of the nectin family of proteins, structurally related to the immunoglobulin superfamily, which serve as intercellular connectors (Campadelli-Fiume et al. 2000). The second step of HSV entry into a cell is fusion of the viral envelope with the plasma membrane of the cell. To effect fusion, gD, when bound to its receptor, recruits glycoproteins B, H and L, which results in fusion of the envelope with the plasma membrane.

Additional understanding of HSV infection has come from recent studies that have lent significance to an old observation that gD interacts with the cation-independent mannose 6 phosphate receptor, contributing to the accumulation of HSV in endosomes. Endocytosis of viral particles results in particle degradation by lysosomal enzymes, but the cells succumb as a consequence of the degradation of cellular DNA by lysosomal DNase. HSV gD blocks this apoptotic pathway to cell death through its interaction with the mannose 6 phosphate receptor. Thus, gD interacts with HveA, nectins, the mannose 6 phosphate receptor, and at least one of the complex of viral glycoproteins involved in the fusion of HSV with the plasma membrane.

In an attempt to target HSV-1 infection to specific cells, a recombinant HSV having a chimeric protein comprising gC and erythropoietin (EPO) on its surface was constructed. Although the recombinant virus bound to cells expressing EPO receptor and endocytosis of the virus occurred, successful infection of these EPO-receptor expressing cells did not occur.

Accordingly, a need continues to exist in the art for viral therapeutic agents exhibiting improved targeting capacities while retaining sufficient capacity to infect to be therapeutically useful. Ideally, suitable viruses would be therapeutic agents, such as oncolytic agents, themselves as well as providing a targeting vehicle or vector for the controlled delivery of polynucleotide coding regions useful as therapeutic agents. Another need in the art is for targeted agents useful in diagnostic applications as, e.g., imaging agents or targeted vehicles for imaging agents.

SUMMARY

The invention satisfies the aforementioned need in the art by providing viral forms suitable for use as therapeutic and diagnostic agents themselves, as well as providing a ready vehicle for the delivery of therapeutic or diagnostic polynucleotide coding regions to cells. These viral forms are modified viruses of the Herpesviridae family of viruses, and are preferably derived from herpes simplex virus type 1 or type 2. The invention provides a method of making virus particles with a novel ligand, and making said particles totally dependent on a receptor of said ligand for entry into targeted cells.

Disclosed herein are methods to modify the surface of, e.g., an HSV virus particle in a manner that targets the virus to a specific receptor present on the surface of a cell of choice, typically a cell in need of therapy or a cell whose presence provides information of diagnostic value. The invention provides viral particles, e.g., HSV particles, having a reduced affinity for their natural cell-surface receptor(s), and methods for producing and using such particles, which minimizes or eliminates the problem of reduced efficiency associated with the mis-targeting of therapeutic and diagnostic viruses. Additionally, the invention provides viral particles, e.g., HSV particles, that exhibit specific affinity for a cell surface component that is not a natural viral receptor and that is present solely or predominantly on a given target cell, as well as methods for producing and using such viruses. Modified viral particles (e.g., HSV) having increased affinity for a cell surface component associated with one or more target cells exhibit improved targeting capabilities relative to prior art viral particles. The modified HSV particles have reduced indiscriminate binding, thereby minimizing sequestration of viral dosages away from the target cells. The invention further provides modified viral particles, such as modified HSV particles, that have both a reduced affinity for natural viral receptors and an increased affinity for a cell surface component associated with a particular target cell(s), with the modified viral particle effectively recruiting that cell surface component for use as a viral receptor. Other benefits of the modified viruses are described herein and will be apparent to those of skill in the art upon review of this disclosure.

In one aspect, the invention provides a recombinant HSV comprising a virus surface protein altered to reduce binding to a sulfated proteoglycan and a gD altered to both reduce binding to one or more of its cellular receptors and to incorporate a heterologous peptide ligand. Preferably gD, or a portion thereof, maintains its membrane fusion properties, but has reduced capacity to bind HveA and/or HveC.

In another aspect, the invention provides a method of targeting an HSV particle to a cell expressing a particular cell surface receptor. Preferably, the cell is a cancer cell, such as a cell in a malignant glioma, and the cell surface receptor is IL13Rα2. In such embodiments, it is preferred that the HSV comprise a gD/IL-13 fusion protein on its surface.

In yet another aspect, the invention provides a method of imaging a cell comprising (a) contacting the cell with a recombinant HSV particle comprising (i) an altered gD forming a fusion with a peptide ligand to a receptor specific to the cell and (ii) a gene encoding a marker protein and (b) detecting the presence of the marker protein.

Another aspect of the invention is a method of killing a target cell, comprising contacting the target cell with a recombinant HSV particle comprising an altered gD forming a fusion with a peptide ligand to a receptor specific to the cell.

Yet another aspect of the invention is a recombinant HSV comprising (a) a first gene encoding an altered viral surface protein, wherein the alteration reduces binding of the viral surface protein to a sulfated proteoglycan; (b) a second gene encoding an altered gD, wherein the alteration reduces binding of gD to one or more of its cellular receptors; and (c) a coding region for a heterologous peptide surface ligand, wherein the coding region of the second gene and the coding region for a heterologous peptide surface ligand together encode a fusion protein comprising the altered gD and the heterologous peptide surface ligand.

Other features and advantages of the invention will be better understood by reference to the brief description of the drawing and the description of the illustrative embodiments that follow.

BRIEF DESCRIPTION OF THE DRAWING

FIG. 2. Amino acid sequence alignment of IL13-gC, IL13-gD junction sequence, and the HS binding domain of gB. FIG. 2A. The amino-terminal sequence of IL13-gC chimeric protein (SEQ ID NO:22). The sequences upstream and downstream of the HS binding site portion are shown. IL13 was inserted between the two restriction enzyme sites that are underlined. FIG. 2B. The domain of the gB open reading frame (i.e., ORF) from which the poly lysine [poly(K)] sequence was deleted (SEQ ID NO:23). The underlined sequences (codons 68-77) were not present in gB amplified from R5107. FIG. 2C. The amino-terminal sequence of IL13-gD (SEQ ID NO:24). The first underlined sequence identifies the gD signal peptide. IL13 (bracketed by arrows) was inserted between residues 24 and 25 (underlined) of gD, between the XhoI and KpnI restriction enzyme sites.

DESCRIPTION OF ILLUSTRATIVE EMBODIMENTS

Figure 1:
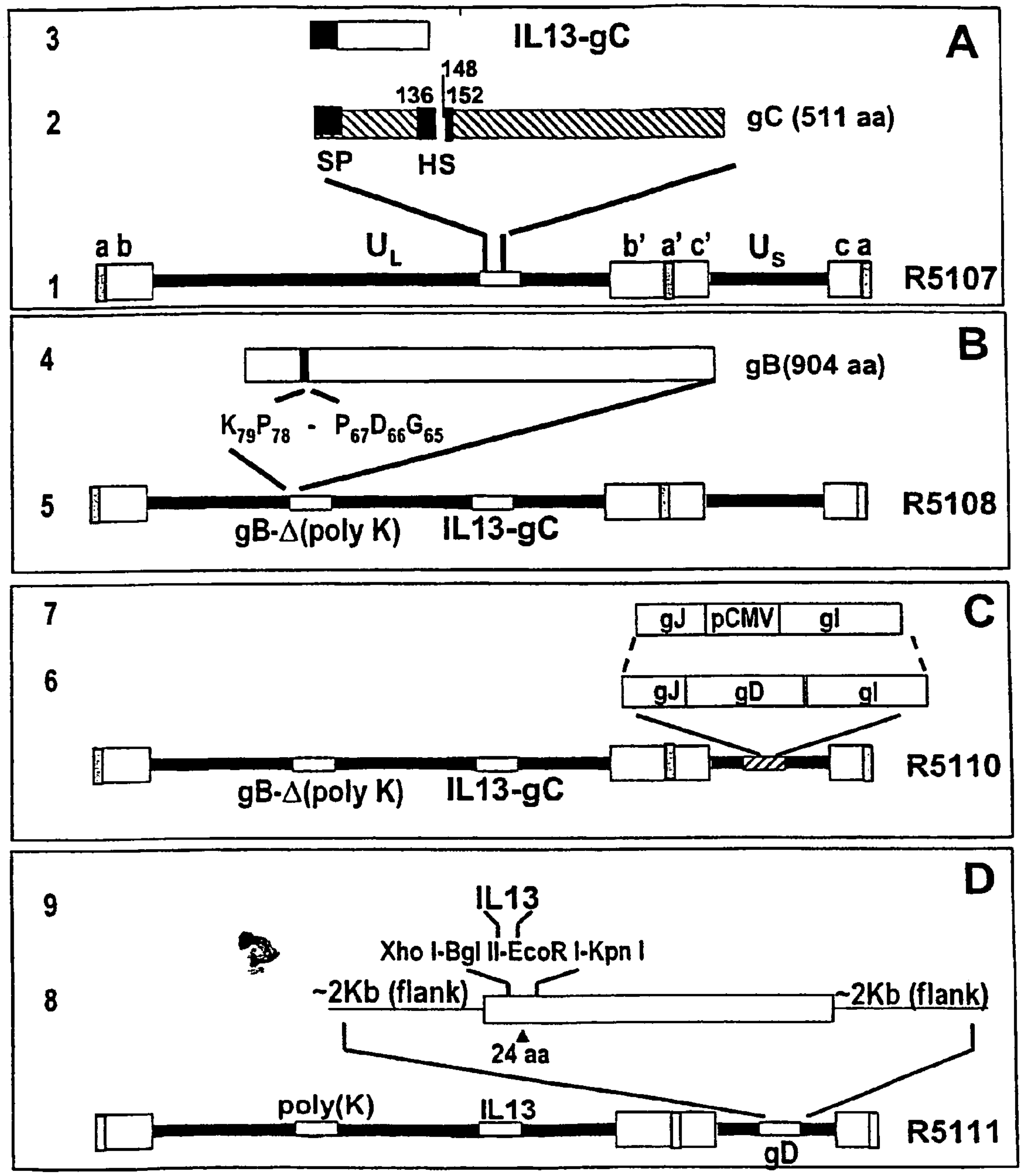
FIG. 1. Schematic representation of the HSV-1 (F) genome and gene manipulations in glycoprotein C (gC), glycoprotein B (gB), and glycoprotein D (gD). Line 1, sequence arrangement of the HSV-1 genome. The rectangular boxes represent the inverted repeat sequences ab and b'a' flanking the unique long ($U_L$) sequence, and inverted repeat c'a' and ca flanking the unique short ($U_S$) sequence. Line 2, sequence arrangement of domains of the glycoprotein C; the signal peptide (SP) domain and heparan sulfate (HS)-binding domain of gC are highlighted. Line 3, human IL13 with signal peptide that replaced the N-terminal segment of 148 amino acids of gC. Line 4, sequence arrangement of the poly-lysine domain of gB. Line 5, schematic representation of a recombinant HSV-1(F) genome, in which the N-terminal domain of gC was replaced with IL13 and the polylysine domain (from codon 68 to codon 77) of gB was deleted. Line 6, sequence arrangement of glycoprotein J (gJ), glycoprotein D (gD), and glycoprotein I (gI) in $U_S$. Line 7, replacement of gD with the immediate early promoter of CMV in order to enable the expression of gI. Line 8, schematic representation of recombinant HSV-1(F) genome, in which the N-terminal domain of gC was replaced with IL13, the poly-lysine domain of gB was deleted, and IL13 was inserted after amino acid 24 of gD. Line 9, a polylinker XhoI-BglII-EcoRI-KpnI was inserted after amino acid 24 of gD, with IL13 inserted into the XhoI and KpnI sites of gD.

The invention provides benefits that will improve the health and well-being of animals such as man by providing a targeted approach to the treatment of a variety of conditions and diseases that currently impair health, resulting in significant economic burdens using conventional treatments. In providing modified viral particles having controllable targeting capacities, the diagnostic and therapeutic benefit of the viruses themselves can be delivered with greater precision to particular cells. Additionally, these viral particles can be used as targeting vehicles for the delivery of a wide variety of therapeutic and diagnostic biomolecules, such as polynucleotides encoding therapeutic or diagnostic peptides.

Beyond the modified viral particles, the invention provides methods for making such therapeutic and diagnostic agents as well as methods for using the agents to diagnose or treat a variety of diseases and conditions, such as tumorigenic disease (e.g., gliomas). To facilitate an understanding of the invention and all of its aspects, illustrative embodiments are described below. The descriptions of these illustrative embodiments are not meant to limit the invention to those embodiments disclosed herein. In light of the description, one of skill in the art will understand that many changes and modifications can be made to the illustrative embodiments and still remain within the invention. The illustrative embodiments are disclosed using as an exemplary virus a member of the Herpesviridae family of viruses, herpes simplex virus, or HSV.

As noted above, HSV-1 and HSV-2 are members of the family of viruses known as the Herpesviridae, whose structures are well known in the art. The targeting methods of the invention are applicable to any member of the Herpesviridae and are not limited to the exemplary embodiments described in the examples. Furthermore, a large number of recombinant HSV viruses are known in the art. Such viruses may contain one or more heterologous genes. Also, such viruses may contain one or more mutated HSV genes, for example, mutations that render the virus replication-deficient or affect the virulence of the virus in one or more cell types.

Examples of recombinant HSV containing a heterologous gene and methods of making and using such viruses are described in U.S. Pat. No. 5,599,691 (incorporated herein by reference in its entirety). Preferred heterologous genes include genes encoding marker proteins. Marker proteins, such as green fluorescent protein, luciferase, and beta-galactosidase, allow detection of cells expressing the protein. In other embodiments, the heterologous gene encodes an enzyme that activates a prodrug thereby killing adjacent uninfected cells. In yet other embodiments, the heterologous gene encodes a protein that affects the immune response, such as interleukin 12 (IL-12). Such proteins that activate the immune response against a tumor are particularly useful.

In one aspect, the invention relates to altering the surface of an HSV particle to target the virus to a specific receptor. By creating a fusion protein comprising a portion of gD and a ligand, the virus is targeted to a cell having a cell surface receptor that binds the ligand. In preferred embodiments, one or more HSV surface proteins, such as gB, gC, or gD, are altered to reduce binding to natural HSV receptors.

A "natural receptor" as used herein is a cell surface molecule that interacts with wild-type HSV in the absence of human intervention. For example, gB and gC of HSV-1 interact with heparan sulfate proteoglycans in a natural infection. In preferred embodiments, gB and/or gC are altered to reduce or eliminate binding to heparan sulfate proteoglycans. As another example, gD is known to bind to several receptors, including HveA and HveC, in a natural infection. In preferred embodiments, gD is altered to reduce or eliminate binding to HveA and/or HveC.

Receptor-ligands

As used herein, "receptor" and "ligand" refer to two members of a specific binding pair and, hence, are binding partners. A receptor is that member of the pair that is found localized on the surface of the cell; the ligand is the member of the pair that is found on the surface of HSV. Thus, in certain embodiments, the "ligand" may actually be what the art recognizes as a receptor outside the context of the invention and the "receptor" may be its respective ligand. Moreover, a "ligand" and a "receptor" as used herein refer to intact molecules or portions of such molecules that retain the capacity to specifically bind to the other member of the binding pair.

One advantage of the invention is the ability to tailor HSV to target a specific receptor while maintaining infectivity of the virus. In an exemplary embodiment, an HSV particle contains a fusion protein comprising a portion of gD and the cytokine IL-13. Such a virus is able to infect cells expressing the receptor IL-13Rα2. Because IL-13Rα2 is expressed on the surface of cells of malignant gliomas, HSV containing the gD/IL-13 fusion protein are effectively targeted to such cells. Ligands that bind to receptors which are overexpressed or differentially expressed on either tumor cells or cells associated with tumor growth (e.g., neovasculature) are particularly preferred. Examples include the $\alpha_v\beta_3$-$\alpha_v\beta_5$ integrins, which are overexpressed in tumor neovasculature; epidermal growth factor receptor (EGFR), which is overexpressed in head, neck, lung, colon, breast, and brain cancer cells; HER-2/Neu, which is overexpressed in breast cancer cells; MUC-1, which is overexpressed in breast, lung, and pancreas cancer cells; and prostate-specific membrane antigen, which is overexpressed in prostate cancer cells. In certain embodiments, the ligand is a single-chain antibody that binds to its cognate specific binding pair member, herein referred to as a receptor. Single-chain antibodies have been shown to be effective in targeting applications, as evidenced by their ability to target retroviruses to specific receptors.

Essentially any two binding pair members or partners may be used as receptor-ligands in the invention. However, it is contemplated that certain factors, such as the distance from the binding site on the receptor to the membrane, or the conformation of the ligand when fused to gD, may affect the efficiency of recombinant HSV fusion to the cell membrane. Therefore, screens for effective receptor-ligand pairs are contemplated, using no more than routine procedures known in the art. Additional screens, conventional in nature, may be used to optimize constructs. One routine method of screening is to follow the protocol provided in the example for candidate receptor/ligand pairs, using IL-13R/IL-13 as a control receptor/ligand pair.

Alternatively, one may use a membrane fusion assay as described in Turner et al., 1998, incorporated herein by reference in its entirety. In the Turner assay, cells transfected with construct(s) encoding gB, gH, gL, and the gD/ligand fusion protein, and cells expressing the receptor, are co-cultured and the cells are examined for membrane fusion. Membrane fusion between gD/ligand-expressing cells and receptor-expressing cells indicates that the candidate receptor-ligand pair (the ligand being a gD/ligand fusion protein) is functional. Constructs encoding functional gD/ligand proteins can then be used to create recombinant HSV that are targeted to cells expressing the receptor.

Cell Targeting

Evident from the preceding discussion, another aspect of the invention is the targeting of a recombinant HSV to a cell having a specific receptor on its surface. In preferred embodiments, a recombinant HSV is designed to comprise a ligand that interacts with a receptor known to be expressed on a cell of interest. The cell of interest is then infected with recombinant HSV. Such targeting methods may be used for a variety of purposes.

In one aspect, a recombinant HSV is used to introduce a heterologous gene into a cell that expresses the receptor. In preferred embodiments, the cell is not infected by, or is poorly infected by, wild-type HSV. Thus, in certain embodiments, the invention provides a vector for transforming a cell of interest with a heterologous gene.

Further, a cell can be rendered a target of a recombinant HSV of the invention. The cell can be rendered a target by transforming the cell to express a receptor capable of specifically binding a ligand expressed on a recombinant HSV of the invention. For example, as described in Example 2, the J1.1 cell line, which was resistant to infection by a recombinant HSV expressing an IL-13 ligand, was rendered susceptible to infection by transforming the cell line with a vector encoding IL12Rα2 to produce the cell line J13R.

In embodiments of the invention designed to treat diseases, disorders, or conditions associated with unwanted or excessive cell proliferation, such as cancer or restenosis, HSV is targeted to proliferating cells thereby killing the cells. Because HSV is lethal to infected cells, expression of a heterologous gene is not required. However, in embodiments wherein the lethality of HSV is attenuated, an HSV harboring a gene that is lethal to the infected cell or that prevents proliferation of the infected cell may be used to target a cell.

Alternatively, HSV targeted to specific surface markers can be used to visualize the distribution of tumor cells in tissues. This diagnostic tool had been unavailable because of the indiscriminate binding of HSV to cells. Modification of HSV by eliminating (ablating) or reducing the indiscriminate binding of HSV to heparan sulfate proteoglycans without deleteriously affecting the capacity of such HSV to replicate in both dividing and non-dividing cells makes possible the use of these modified viral forms to visualize the distribution of tumor cells.

In one preferred method for visualizing the distribution of tumor cells, radioactive visualization is achieved by viral thymidine kinase (TK)-dependent incorporation of a radioactive precursor. Methods of molecular imaging of gene expression are well known in the art. Methods often use highly sensitive detection techniques such as positron emission tomography (PET) or single-photon emission-computed tomography (SPECT). In one embodiment, TK expression is measured using a gancyclovir analog, such as 9-(3-[$^{18}$F]fluoro-1-hydroxy-2-propoxy)methylguanine, as the tracer or marker (Vries et al., 2002). For a review of imaging TK gene expression using PET or SPECT, see Sharma et al., 2002 or Vries et al., 2002.

A second preferred imaging method is to fuse a non-critical tegument protein (e.g. $U_S11$, which is present in nearly 2000 copies per virus particle) to a marker protein, such as green fluorescent protein, which is capable of being visualized in vivo. Alternatively, a non-critical protein can be fused to a luciferase and the presence of the luciferase visualized with a luminescent or chromatic luciferase substrate. Although a marker protein can be fused to essentially any viral structural protein, preferred viral proteins include gC, gE, gI, gG, gJ, gK, gN, $U_L11$, $U_L13$, $U_L14$, $U_L21$, $U_L41$, $U_L35$, $U_L45$, $U_L46$, $U_L47$, $U_L51$, $U_L55$, $U_L56$, $U_S10$, and $U_S11$. The marker protein also may be fused to thymidine kinase (Soling et al., 2002).

Library Screening

As noted above, HSV comprising a gD/ligand fusion protein can bind and infect cells expressing a receptor to the ligand. In one embodiment, a cell line expressing a receptor is used in screening for ligands of the receptor. cDNA from a cDNA library is cloned into a vector encoding a portion of gD to produce a gD/cDNA-encoded fusion protein. The resulting vectors are then screened for membrane fusion using the assay of Turner et al. described above or by creating recombinant HSV expressing the gD/cDNA-encoded fusion protein and screening the viruses for the ability to infect receptor-expressing cells. Such methods may be used, e.g., to identify a ligand to an orphan receptor.

In other embodiments, mutations in, or variants of, the receptor or ligand are screened to determine whether the mutants or variants maintain the ability to interact with the respective partner. Such methods may be useful in determining the specific residues important in receptor-ligand interaction.

Therapeutic Methods

Another aspect of the invention is the use of the targeted HSV in therapeutic methods. By altering the cell-binding and infectivity properties of the virus, many routes and methods of administration become viable. For example, non-targeted HSV will bind indiscriminately to a variety of cells. Because of this property, large virus numbers are used and intravenous administration is generally not effective. However, by targeting the virus, one may lower the viral load (i.e., quantity of virus), yet maintain or increase efficacy. Furthermore, the targeted HSV can be administered intravenously and produce therapeutic effects.

Therapeutic methods of the invention include those methods wherein an HSV is targeted to a receptor of a cell that contributes to, or is the basis of, a disease or disorder. These targeted HSV can either exploit the therapeutic properties of HSV itself (e.g., the lethality of HSV to infected cells) or the targeted HSV can serve as a vector for the targeted delivery of at least one therapeutic polynucleotide, such as an expressible polynucleotide comprising a coding region. For example, in methods wherein the targeted HSV contains one or more gene products that render the virus toxic to the cell or that prevent or inhibit cell proliferation, a preferred receptor is overexpressed or selectively expressed on harmful or undesirable cells, such as cancer cells. In other embodiments, the targeted HSV encodes a gene product that provides a desired function or activity in the targeted cell, e.g., when a cell has one or more genetic defects preventing the cell from functioning properly.

In some embodiments, a targeted HSV composition of the invention is delivered to a patient at or around the site of a tumor, which is a very efficient method for counteracting clinical disease. Alternatively, systemic delivery of targeted HSV compositions may be appropriate in other circumstances, for example, where extensive metastasis has occurred, or where inaccessible tumors are encountered.

It is contemplated that in certain embodiments of the invention a protein that acts as an angiogenesis inhibitor is targeted to a tumor. Also, an angiogenesis inhibitor agent may be administered in combination with a targeted HSV of the invention. These agents include, for example, Marimastat (British Biotech, Annapolis Md.; indicated for non-small cell lung, small cell lung and breast cancers); AG3340 (Agouron, LaJolla, Calif.; for glioblastoma multiforme); COL-3 (Collagenex, Newtown Pa.; for brain tumors); Neovastat (Aeterna, Quebec, Canada; for kidney and non-small cell lung cancer) BMS-275291 (Bristol-Myers Squibb, Wallingford Conn.; for metastatic non-small cell lung cancer); Thalidomide (Celgen; for melanoma, head and neck cancer, ovarian, and metastatic prostate cancers; Kaposi's sarcoma; recurrent or metastatic colorectal cancer (with adjuvants); gynecologic sarcomas, liver cancer; multiple myeloma; CLL, recurrent or progressive brain cancer, multiple myeloma, and non-small cell lung, nonmetastatic prostate, refractory multiple myeloma, and renal cancer); Squalamine (Magainin Pharmaceuticals Plymouth Meeting, PA; non-small cell lung cancer and ovarian cancer); Endostatin (EntreMEd, Rockville, Md.; for solid tumors); SU5416 (Sugen, San Francisco, Calif.; recurrent head and neck, advanced solid tumors, stage III or IV breast cancer; recurrent or progressive brain (pediatric) cancer; ovarian cancer, AML (acute myeloid leukemia); glioma, advanced malignancies, advanced colorectal cancer, von-Hippel Lindau disease, advanced soft tissue cancer; prostate cancer, colorectal cancer, metastatic melanoma, multiple myeloma, malignant mesothelioma: metastatic renal, advanced or recurrent head and neck cancer, metastatic colorectal cancer); SU6668 (Sugen San Francisco, Calif.; advanced tumors); interferon-α; Anti-VEGF antibody (National Cancer Institute, Bethesda Md.; Genentech San Franscisco, Calif., for refractory solid tumors; metastatic renal cell cancer, in untreated advanced colorectal cancer; EMD121974 (Merck KCgaA, Darmstadt, Germany, for HIV-related Kaposi's sarcoma, and progressive or recurrent Anaplastic Glioma); Interleukin 12 (Genetics Institute, Cambridge, Mass., for Kaposi's sarcoma) and IM862 (Cytran, Kirkland, Wash., for ovarian cancer, untreated metastatic cancers of colon and rectal origin, and Kaposi's sarcoma). The. parenthetical information following the agents indicates the cancers against which the agents are being used in these trials. It is contemplated that any of these disorders may be treated with the targeted HSV compositions of the invention, either alone or in combination with the agents listed.

In order to prepare a therapeutic composition for clinical use, it will be necessary to prepare the therapeutic composition as a pharmaceutical composition, i.e., in a form appropriate for in vivo applications. Generally, this will entail preparing compositions that are essentially free of pyrogens, as well as other impurities that could be harmful to humans or other vertebrates.

Generally, appropriate salts and buffers are included to render delivery vectors stable and to allow for uptake by target cells. Aqueous compositions of the invention comprise an effective amount of the targeted HSV, dissolved or dispersed in a pharmaceutically acceptable carrier or aqueous medium. Such compositions also are referred to as inocula. The phrase "pharmaceutically acceptable" or "pharmacologically acceptable" refer to molecular entities and compositions that do not produce adverse, allergic, or other untoward reactions when administered to an animal or a human. As used herein, "pharmaceutically acceptable carriers" includes any and all solvents, dispersion media, coatings, antibacterial and antifungal agents, isotonic and absorption delaying agents, and the like. The use of such media and agents for pharmaceutically active substances is well known in the art. Unless a conventional medium or agent is incompatible with either the vectors of the invention or the intended subject receiving treatment, its use in therapeutic compositions is contemplated. Supplementary active or inert ingredients also can be incorporated into the compositions.

The active compositions of the invention include standard pharmaceutical preparations. Administration of these compositions according to the invention is by any known route, provided that the target tissue is accessible via that route. The pharmaceutical compositions may be introduced into the subject by any conventional method, e.g., by intravenous, intradermal, intramusclar, intramammary, intraperitoneal, intrathecal, retrobulbar, intravesicular, intrapulmonary (e.g., term release); sublingual, nasal, anal, vaginal, or transdermal delivery, or by surgical implantation at a particular site. The treatment may consist of a single dose or a plurality of doses over a period of time.

Upon formulation, solutions are administered in a manner compatible with the dosage formulation and in such amount as is therapeutically effective. Appropriate dosages may be ascertained through the use of established routine assays. As studies are conducted, further information will emerge regarding optimal dosage levels and duration of treatment for specific diseases, disorders, and conditions.

In preferred embodiments, the unit dose may be calculated in terms of the dose of viral particles being administered. Viral doses are defined as a particular number of virus particles or plaque forming units (pfu). Particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10- to 100-fold) due to the presence of infection-defective particles, which is determinable by routine assays known in the art.

The pharmaceutical compositions and treatment methods of the invention are useful in the fields of human medicine and veterinary medicine. Thus, the subject to be treated may be a vertebrate, e.g., a mammal, preferably human. For veterinary purposes, subjects include, for example, farm animals such as cows, sheep, pigs, horses and goats, companion animals such as dogs and cats, exotic and/or zoo animals, laboratory animals including mice, rats, rabbits, guinea pigs and hamsters; and poultry such as chickens, turkey, ducks and geese.

In some embodiments of the invention, it is contemplated that the targeted HSV is administered in conjunction with chemo- or radiotherapeutic intervention, immunotherapy, or with any other therapy conventionally employed in the treatment of cancer.

To kill cells, inhibit cell growth, inhibit metastasis, inhibit angiogenesis or otherwise reverse or reduce malignant phenotypes using the methods and compositions of the invention, one contacts a "target" cell, a tumor, or its vasculature with a targeted HSV composition and at least one other agent. The components of these compositions are provided in a combined amount effective to kill or inhibit proliferation of cancer cells. This process may involve contacting the cells with the targeted HSV composition and the agent(s) or factor(s) at the same time. This may be achieved by contacting the subject organism, or cell of interest, with a single composition or pharmacological formulation that includes both agents, or by contacting the cell with two distinct compositions or formulations, at the same or different times, wherein one composition includes a targeted HSV composition of the invention and the other composition includes the second agent.

Another aspect of the invention provides diagnostic methods that involve imaging a tumor or diseased tissue using a targeted HSV. Such methods are useful in diagnosing a patient with a disease, disorder, or condition that is indicated by the presence of a receptor on the surface of a cell. Diagnostic imaging methods are discussed above.

Kits

Kits according to the invention may include recombinant viruses of the invention or may include vectors for producing such recombinant viruses. A vector for producing a recombinant virus of the invention may encode the gD/ligand fusion protein or may be designed to facilitate cloning of a ligand to produce a gD/ligand fusion protein (e.g., a vector containing a multiple cloning site within the gD coding region that facilitates in-frame insertions).

Other components that can be included in a kit of the invention include a receptor-expressing cell line (useful as a control), a nucleic acid molecule for expressing the receptor in a particular cell type, and instructions for using the kit to effect diagnostic analyses or therapeutic treatments. In certain embodiments, a therapeutic kit will further contain a component for bringing about a therapeutic effect, such as a prodrug or a toxic compound. In other embodiments, a diagnostic kit will contain a compound useful in imaging methods, such as a chromophore or fluorophore, or an antibody for detecting infected cells.

Having provided a general description of the various aspects of the invention, the following disclosure provides examples illustrative of the invention, wherein Example 1 describes construction of a targeted HSV, Example 2 illustrates the construction of a cell line expressing a targeted HSV, and Example 3 describes the controlled infection of a desired cell by a targeted HSV.

EXAMPLE 1

Construction of HSV Targeting Vector R5111

A targeted HSV was constructed to target the recombinant virus to cells of malignant gliomas. The target for entry of the virus into such cells is the IL13Rα2 receptor known to be present in malignant gliomas. Unlike the more prevalent IL13αR1 receptor, the IL13Rα2 receptor has a shorter cytoplasmic domain and does not interact with IL4, of which IL13 is a close relative. In general, the construction of the targeted HSV involved mutagenizing gB and gC to preclude their interaction with heparan sulfate. Also, IL13 was inserted into gD at amino acid 24 thereby disrupting the gD binding site for HveA. The resulting IL13-gD chimeric virus can use IL13Rα2 for entry into cells carrying that receptor.

More specifically, the targeted HSV R5111 was constructed in several steps depicted in the four panels of FIG. 1 and detailed below.

(i) Substitution of amino terminal domain of gC with IL13 fused to the signal sequence of gC. FIG. 1A, lines 1-3 schematically depicts a cDNA consisting of the IL13 coding sequence fused at its amino terminus to its signal sequence. The complete cDNA of IL 13, with the N-terminal signal peptide coding region, was amplified using the PCR primer elongation method. The primers were as follows:

pIL13F1,
CATTGCTCTCACTTGCCTTGGCG-GCTTTGCCTCCCCAGGCCCTGTGCCTC-CCTCTACAGC (SEQ ID NO:1);

pIL13F2,
GCAGCTAGCCTCATGGCGCTTTTGT-TGACCACGGTCATTGCTCTCACTTGCCT-TGGCGGC (SEQ ID NO:2);

and pIL13REcoRI,
GAGCTCGGATCCTGAATTCAACCGTCCCTC (SEQ ID NO:3).

First-round PCR used pIL13F1 and pIL13REcoRI as primers, with pRB5830 (containing the IL13 coding region) as the template. The PCR reaction mixture was then diluted 10-fold and 1 μl of the diluted reaction mixture was used as template for the second round of PCR amplifications with pIL13F2 and pIL13REcoRI as the primer set. The PCR product was gel-purified, digested with NheI/EcoRI, and ligated into pBluescript II KS(+) at XbaI/EcoRI sites to generate pRB5832. To construct the transfer plasmid pRB5835, a 4.8-kbp HindIII/SacI fragment containing the HSV-1 gC coding region was released from cosmid pBC1007 and inserted into pBluescript II KS(+) to generate pRB5833. pRB5833 was cleaved with NheI and EcoRI and the N-terminal 148 residues of gC were replaced with the gC-signal/IL13 chimeric sequence (pRB5834). The insert in pRB5834 was released by XhoI/SacI digestion and ligated into pKO5Y at the same sites to generate pRB5835.

The recombinant virus R5107 (FIG. 1A, line 1) carrying the IL13-gC chimera was generated with the aid of the BAC-HSV system. RR1 competent cells that harbored bacterial artificial chromosome (BAC)-HSV bacmids were transformed with the transfer plasmid pRB5835 by electroporation. After incubation for 1 hour at 30° C. in LB broth, the transformed bacteria were plated on pre-warmed Zeocine (Zeo) plus chloramphenicol (Cm) (20 μg/ml of each) plates and incubated overnight at 43° C. for integration. The next day, six colonies were picked and each was separately diluted in 1 ml LB. Five μl of the diluted bacteria were then plated on Cm/10% sucrose (Suc) plates, and incubated at 30° C. overnight. To further confirm the loss of the replacement vector, 24 Cm/Suc-resistant colonies (four colonies from each plate) were restreaked in duplicate on Cm LB and Zeo LB plates, respectively. The $Suc^r/Cm^r/Zeo^r$ colonies were further screened by PCR (95° C., 4 minutes for cycle 1; then 35 cycles of 94° C., 1 minute; 60° C., 1 minute; and 72° C., 1 minute). The primers were:

pgC-F,
GACACGGGCTACCCTCACTATCGAGGGC (SEQ ID NO:4; from nt 96158 to 96185 in HSV-1 strain 17), and pgC-R,
GGTGATGTTCGTCAGGACCTCCTCTAGGTC (SEQ ID NO:5; from nt 96859 to 96830 in HSV-1 strain 17).

The DNA fragment amplified from PCR-positive clones (FIG. 2B) was sequenced to further confirm the integration of IL13 in the correct open reading frame (ORF) of gC. To verify the viability of the recombinant (R5607), the recombinant BAC-HSV DNA was prepared as described elsewhere (Ye et al., 2000) and transfected into rabbit skin cells by Lipofectamine reagent (Life Technologies, Grand Island, N.Y.). The resultant virus, R5607, was stored at −80° C.

(ii) Deletion of the polylysine track from gB, FIG. 1 panel B. To make a transfer plasmid for the deletion of the gB heparan sulfate binding domain (polylysine), a 4.76 kbp BstEII fragment (from nt 53164 to 57923 of HSV-1) containing the $U_L27$ (gB) ORF released from cosmid BC1014 was blunt-ended and cloned into pBluescript II KS (+) at a SmaI site to generate pRB5846. To construct pRB5847, from which the 10-amino-acid polylysine domain of gB was deleted, two fragments flanking the polylysine domain were amplified by PCR from pRB5846. The primer sets were:

pgB1BamHI:
GTTCTTCTTCGGTTTCGGATCCCCCG (SEQ ID NO:6);

pgB2BspEI:
CGGCATTTCCGGAATAACGCCCACTC (SEQ ID NO:7);

and pgB3BamHI:
CAGAAAACCGGATCCCCCAAAGCCGCC (SEQ ID NO:8);

pgB4BsiWI:
GCCAACACAAACTCGTCGTACGGGTAC (SEQ ID NO:9).

PCR amplified fragments were then cut with BspEI/BamHI, or BsiWi/BamHI and ligated into pRB5846, which had the 1.2 kbp BsiWI/BspEI fragment already deleted. To generate the transfer plasmid pRB5848, the 4.76 kbp insert in pRB5847 was released by XbaI/EcoRV digestion and ligated into pKO5Y at the sites of XbaI and ScaI. Recombinant HSV-1 virus R5108 is based on R5107 with the additional deletion of the gB heparan sulfate binding domain. It was made by the same procedure as BAC-R5607, except that the transfer plasmid pRB5848 was used instead of BAC-HSV wild-type and pRB5835. The sequence of the mutant gB was verified by sequencing the entire ORF.

Figure 6:
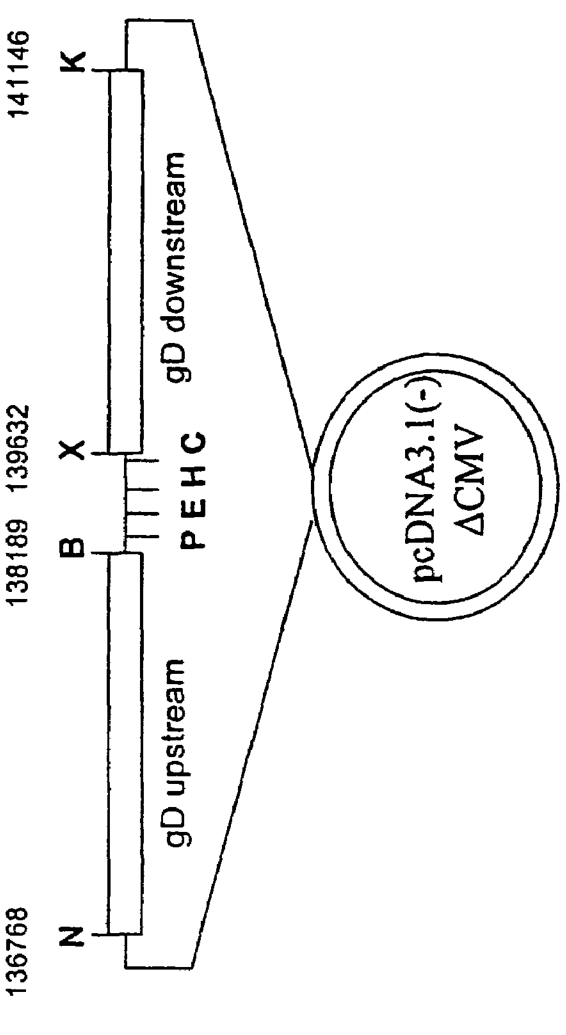
FIG. 6. Diagram of the pgD-vector.

(iii) Deletion of gD (FIG. 1 panel C, lines 6 and 7). The coding sequence of gD was replaced with the human cytomagolovirus immediate early promoter to enable the expression of glycoprotein I. A 0.65 kbp fragment containing the promoter was released from pRB5836 by ClaI digestion and inserted into pgD⁻ (FIG. 6), a plasmid obtained from G. Campadelli-Fiume. This plasmid, containing the flanking sequences of gD but lacking the gD ORF, had been cut with ClaI to generate pRB5849. pRB5849 was then cut with NotI and PmeI and ligated into pKO5Y at the NotI and ScaI sites to generate the transfer plasmid pRB5850. Recombinant HSV-1 virus R5110 is based on R5608 with the additional deletion of gD. It was made by the same procedure as BAC-R5607 except that transfer plasmid pRB5850 was used instead of BAC-HSV wild-type and pRB5835. The recombinant BAC-HSV DNA was prepared as described in (Ye et al., 2000). The mutant virus was designated R5110.

(iv) Construction of the R5111 mutant carrying the IL-13-D chimeric gene (FIG. 1 panel D). Plasmid pRB123 carries a 6,584 bp BamHI J fragment containing the gD coding region and flanking sequences in the BamHI site of pBR322. To construct the IL 13-gD chimeric plasmid, pRB123 was digested with AflII and HpaI to release two fragments of 7.6 kb and 3.2 kb. The 3.2 kb fragment was further digested with FspI to release 2.5 kb and 0.7 kb fragments that contain the amino-terminal 661 bp of the gD ORF. A polylinker sequence containing the restriction sites XhoI-BglIIH-EcoRI-KpnI was inserted into the 0.7 kb fragment downstream of the 24th codon of gD by two PCR reactions using a first forward primer,
5'-CAGTTATCCTTAAGGTCTCTTTTGTGTGGTG-3' (SEQ ID NO: 10), and a first reverse primer,
5'-CCGGAATTCCGGAGATCTTCCCTCGAG-GACCGGAAGGTCTTTGCCGCGAAAG-3' (SEQ ID NO:11), and a second forward primer,
5'CCGGAATTCCGGGGTACCCTGGAC-CAGCTGACCGACCCTCCGG-3' (SEQ ID NO:12), and a second reverse primer,
5'-CGGGGGGATGCGCAGCGGGAGGGCGTACTTAC-3' (SEQ ID NO: 13), respectively. After digestion of the two PCR products by EcoRI, they were ligated and amplified by PCR again to obtain the desired DNA fragment containing the polylinker insertion.

IL13 was amplified by PCR with the forward primer,
5'-CCGCTCGAGATGGCGCTTTTGTTGACCACGG-3' (SEQ ID NO: 14), and the reverse primer,
5'-GGGGTACCGTTGAACCGTCCCTCGCGAAA-3' (SEQ ID NO:15), and then inserted into the XhoI and KpnI sites of the 0.7 kb fragment described above. This new fragment with the IL13 insertion was then ligated with the 2.5 kb and 7.6 kb fragments (see above) to generate the IL13-gD chimeric transferplasmid, pRB13-24.

R5111 was generated by co-transfection of transfer plasmid pRB13-24 and the R5110 viral DNA into U87 glioma cells. The progeny of the transfection was plated at a high dilution on Vero and HEp-2 cell cultures to yield individual, well-spaced plaques. From each of the infected cell cultures, six single plaques were picked, frozen-thawed, sonicated, and then replated on fresh cultures of Vero or HEp-2 cells (depending on the origin of the plaque) for preparation of virus stocks and to prepare viral DNA for sequencing.

Viral DNA extraction. Infected cells were removed from each of the 25 $cm^2$ flasks exposed to individual plaque isolates, rinsed, and resuspended in 500 μl of Lyse-O-Lot (150 mM NaCl, 10 mM Tris, 1.5 mM $MgCl_2$ in the presence of 0.1% of NP40). Nuclei were removed by low-speed centrifugation. To the supernatant fluid were added sodium dodecyl sulfate (SDS) to 0.2%, EDTA to 5 mM and β-ME to 50 mM. The solution was then extracted twice with phenol/chloroform. Viral DNA was finally precipitated by ethanol, resuspended, and the IL13 ORF and IL13-gD chimeric reading frame were amplified by PCR with two sets of primers. The first set, designed to amplify IL13, consisted of: a forward primer, 5'-CCGCTCGAGATGGCGCTTTTGTTGACCACGG-3' (SEQ ID NO:16), and a reverse primer, 5'-GGGGTACCGTTGAACCGTCCCTCGCGAAA-3' (SEQ ID NO:17), which will amplify the IL13 ORF. The second set, designed to amplify the IL13-gD junction, consisted of a forward junction primer, 5'-CCGCTCGAGATGGCGCTTTTGTTGACCACGG-3' (SEQ ID NO:18), and a reverse junction primer, 5'-AACTGCAGGTTGTTCGGGGTGGCCGGGGG-3' (SEQ ID NO:19). All 12 IL13-gD PCR products were sequenced to determine whether the gD sequence contained deletions or substitutions.

Verification of the structure of R5111 The construction of the R5111 virus is depicted in FIG. 1. The design involved replacement of the HveA binding site with the IL13 ligand to enable the recombinant virus to bind the IL13α2 receptor on cell surfaces and to delete the sequences reported to bind to heparan sulfate. Verification of the structure of R5111 was done as follows:

(i) The replacement of the amino-terminal domain of gC with IL13 and the disruption of the heparan sulfate binding site was initially verified by sequencing gC from recombinant R5107 (FIG. 2A).

(ii) The deletion of codons 68-77 of gB was verified by sequencing the gB ORF amplified by PCR from recombinant R5108 (FIG. 2B).

Figure 3:
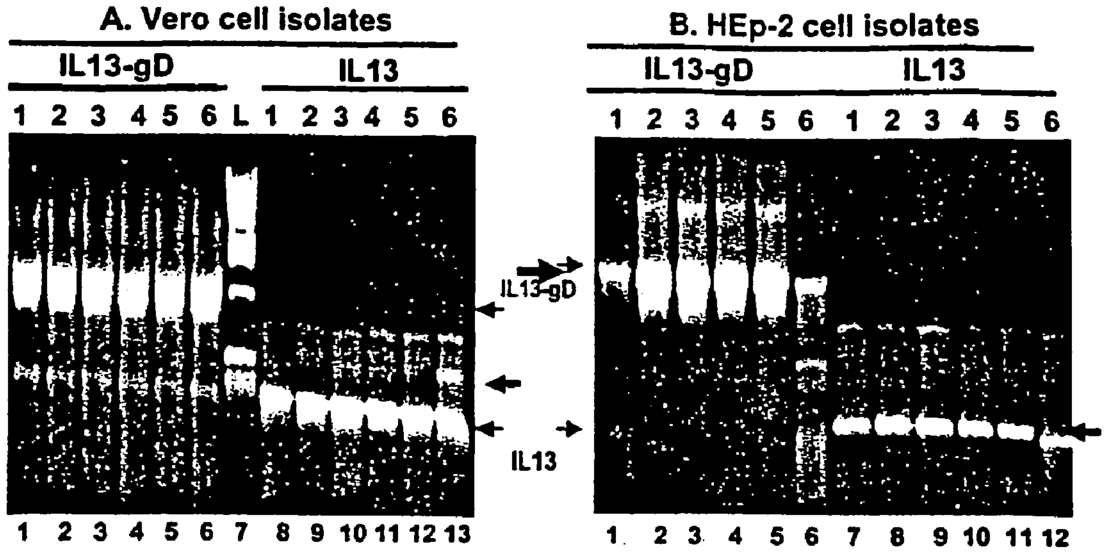
FIG. 3. Verification of R5111 viral DNA by PCR. Photographs of electrophoretically separated PCR products amplified directly from the plaques picked from Vero (FIG. 3A) and HEp-2 (FIG. 3B) cells. Viral DNAs were extracted as described in Example 1 and subjected to PCR with "IL13" primers from the IL13 ORF and IL13-gD primers, which bracketed IL13 and the gD ectodomain.

(iii) The presence of chimeric IL13-gD in R5111 was verified by PCR, as illustrated in FIG. 3, and by sequencing the entire IL13-gD coding region, amplified by PCR, as shown in FIG. 2. The R5111 recombinant was initially isolated from transfected U87 cells and grown in parallel in Vero cells and HEp-2 cells. To determine whether the virus grown in Vero cells or HEp-2 cells differed with respect to amino acid sequence, six plaques each from Vero or HEp-2 cultures containing well-separated plaques were picked. In this series of verification experiments, two sets of primers were used to confirm the presence of the IL13 insert in gD and to verify the presence of a junction between IL13 and gD. In a second round of verifications, the 12 clones of gD were sequenced to determine whether the isolates obtained from the viruses passaged in Vero cells or in HEp-2 cells differed in amino acid sequence. No differences were found. Furthermore, except for the inserted IL13 sequence, no differences were found between the sequence of HSV-1 (F) gD and those of the cloned IL-13-gD chimeric genes (FIG. 2C).

Figure 4:
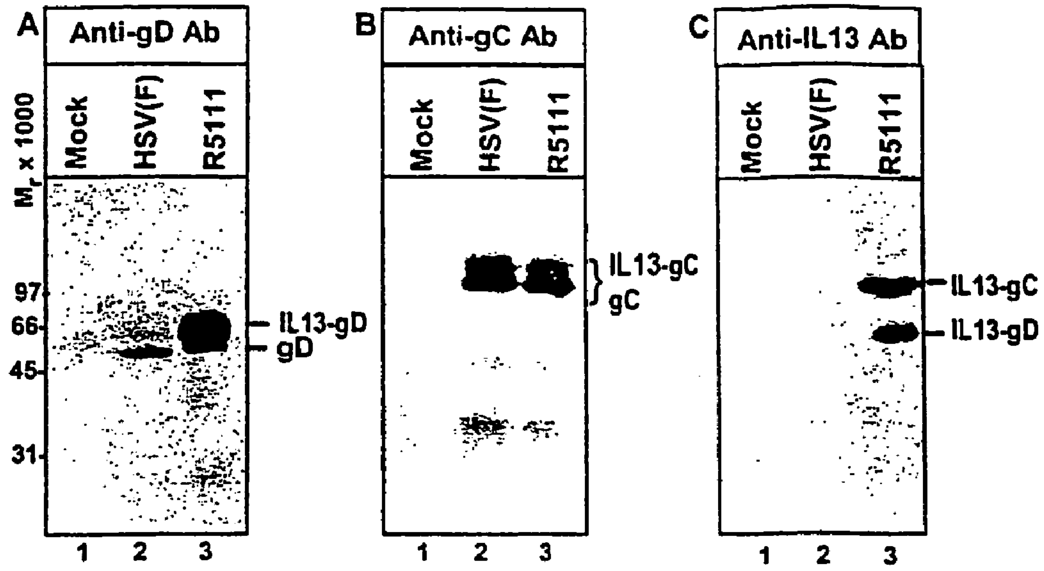
FIG. 4. Photograph of electrophoretically separated proteins from lysates of cells infected with R5111 reacted with antibody to gC, gD or IL13. HEp-2 cells grown in 25 $cm^2$ flasks were exposed to 10 PFU of HSV-1 or R5111 per cell. The cells were harvested 24 hours after infection, solubilized, subjected to electrophoresis in 10% denaturing polyacrylamide gels, electrically transferred onto a nitrocellulose sheet, and exposed to a monoclonal antibody against gD (FIG. 4A), gC (FIG. 4B) or IL13 (FIG. 4C), respectively. The protein bands corresponding to the gC, IL13-gC fusion protein, gD and the IL13-gD fusion protein are indicated. IL13-gC was the same size as native gC, as expected.

(iv) In denaturing polyacrylamide gels, IL13 migrated as a protein with an apparent Mr of 15-17,000. In the recombinant R5111, IL13 replaced 148 amino acids of gC. FIG. 4B shows an immunoblot of electrophoretically separated proteins from a lysate of R5111 mutant-infected cells exposed to an antibody to gC. As illustrated in that figure, the anti-gC antibody reacted with proteins present in lysates of HSV-1 (F) and with proteins from R5111 lysates, exhibiting similar electrophoretic mobilities. In contrast, an antibody to IL13 reacted with a band of similar mobility in R5111 lysates (FIG. 4C, lane 3) but not in lysates of HSV-1 (F) (FIG. 4C, lane 2). The IL13-gD fusion protein in the R5111 mutant virus was verified by reacting the cell lysates with gD and IL13 antibody. Comparison of wild-type gD and the chimeric IL13-gD chimeric protein (FIG. 4A, lane 3), showed that, as expected, IL13-gD migrated more slowly than the wild-type gD (FIG. 4A, lane 2). The faster migrating band of gD did not react with the antibody to IL13 (FIG. 4C, lane 2).

EXAMPLE 2

Construction of a Cell Line Expressing the IL13 Receptor (IL13Rα2)

A rigorous test of the ability of R5111 to utilize the IL13Rα2 protein as a receptor for entry required construction of a cell line expressing IL13Rα2 in the absence of other HSV-1 entry receptors. The J1.1 cell line was selected for this construction. In essence, this cell line lacks the receptors necessary for the entry of virus into cells and the cell line is not susceptible to infection by wild-type virus. The construction of a plasmid encoding a IL13Rα2 protein fused at its carboxyl terminus to a HA tag, transfection of J1.1 cells with the plasmid encoding the tagged ILRα2 protein, and selection of the cell line expressing the protein is described below.

To test for the production of IL13Rα2 protein, five clones of the selected cells were harvested, solubilized, subjected to electrophoresis in denaturing polyacrylamide gels and tested for expression of the protein.

Construction of J13R, a cell line stably expressing IL13Rα2 receptor. The IL13α2 coding region was tagged with an HA tag at its 3' end (the carboxyl terminus of the encoded polypeptide) by PCR with forward primer, 5'-AAGATTTGGGCTAGCATGGCTTTCGTTTGC-3' (SEQ ID NO:20), and reverse primer, 5'-TCCCTCGAAGCTTCAAGCATAATCTGGCACATCATATGTATCACAGAAAAA-3' (SEQ ID NO:21). NheI and HindII restriction digests were used to create compatible ends. The DNA fragment was then inserted into pcDNA 3.1 (zeo) vector (Invitrogen; Carlsbad, Calif.) to generate transfer plasmid pRB13-R2. All of the constructs were sequenced to insure fidelity.

J1.1, a derivative of BHK thymidine kinase[31] cells which lack both HveA and nectin 1 receptors, was obtained from Dr. G. Campadelli-Fiume, University of Bologna, Italy. J1.1 cells, stably transfected with pRB 13-R2 using a Lipofectamine kit (Gibco-BRL), were selected on the basis of their resistance to zeocin (Invitrogen). Zeocin-resistant clones were amplified and screened for IL13Rα2 expression by immunobloting with anti-HA polyclonal antibody. Lysates of parental and transformed cells formed by solubilized in SDS were each electrophoretically separated in a denaturing gel (50 kg/lane), transferred to a nitrocellulose sheet, and probed with antibody against HA (Santa Cruz Biotechnology). The protein bands were visualized by an enhanced chemiluminescent detection (ECL) system (Pierce, Rockford, Ill.) according to the instructions of the manufacturer. One (J13R-2) was selected for testing the ability of R5111 to use the IL13Rα2 receptor.

Figure 5:
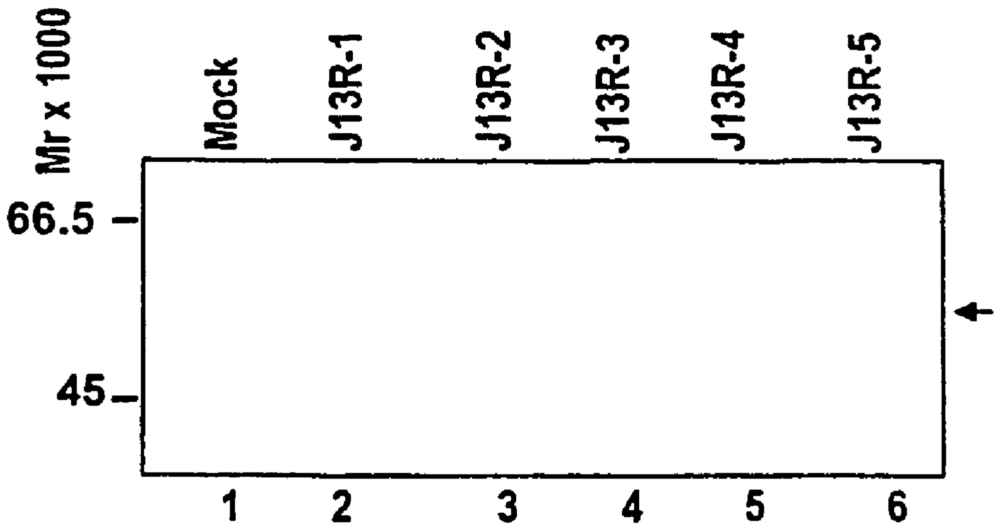
FIG. 5. HA-tagged IL13Rα2 expression from individual clones of stable transfectants of the J1.1 cell line. The individual clones were amplified as described in Example 1. Cells were harvested from 25 $cm^2$ flasks, solubilized, and subjected to electrophoresis in 12% denaturing polyacrylamide gels, electrically transferred onto a nitrocellulose sheet, and exposed to a polyclonal antibody to HA tag.

As shown in FIG. 5, all clones expressed a protein band reactive with the anti-HA antibody. The apparent size of the protein was consistent with the reported size of IL13Rα2. Of 5 J13R-positive clones, J13R-2 (FIG. 5, lane 3) was selected and designated J13R.

EXAMPLE 3

Infection by the HSV Targeting Vector R5111

SK-N-SH, HEp-2, Vero, and U87 cells were obtained from American Type Culture Collection (Rockville, Md.) and maintained in Dulbecco's modification of Eagle's Minimal Essential Medium (DMEM) supplemented with 10% fetal bovine serum. Replicate cultures of SK-N-SH, HEp-2, Vero, U87, J1.1, and J13R were exposed to 0.01 PFU of R5111 virus per cell. After 24 hours of incubation, the cells were harvested and viral yields were titered on Vero cells.

Immunoblotting electrophoretically separated proteins. The indicated cells were mock-infected or exposed to 10 PFU of recombinant or wild-type HSV-1(F) per cell. The cells were harvested at 24 hours after infection, disrupted in SDS disruption buffer, boiled, cleared by centrifugation and electrophoretically separated on a 10% denaturing polyacrylamide gel. After transfer to a nitrocellulose membrane, the isolated proteins were reacted with antibodies as indicated using known and conventional techniques. Monoclonal antibodies against gD- (clone H170), gC- and HA-specific polyclonal antisera were purchased from the Goodwin Institute, Plantation, Fla. Polyclonal antibodies against IL13 were purchased from Santa Cruz Biotechnology.

The results shown in Table 1 were as follows: R5111 replicated to within a 10-fold range in HEp-2, Vero, U87, and J13R cells. The titer obtained from J1.1 cells was approximately $10^5$-fold lower than that obtained from all other cell lines. To test whether the J13R cell line had acquired a receptor for wild-type HSV-1 (HSV-1(F)), J1.1 and J13R cells were also exposed to the wild-type virus. The results, also shown in Table 1, indicate that the cells remain resistant to the wild-type virus. It was known that HEp-2 cells express the nectin receptor but not the HveA receptor. The results show that the targeted HSV containing an IL13-gD fusion can target (i.e., bind and infect) cells expressing a particular receptor (IL13Rα2) approximately as well as wild-type HSV targets cells expressing the HveA receptor. The results indicate that R5111 can use IL13Rα2 as a receptor for entry in a cell line lacking all other HSV-1 receptors.

TABLE 1

Replication of R5111 in various cell lines

| Virus | Cell Line* | Yield** |
|---|---|---|
| R5111 | Vero | $11 \times 10^7$ |
| | HEp-2 | $1.2 \times 10^7$ |
| | SK-N-SH | $17 \times 10^7$ |
| | U87 | $27 \times 10^7$ |
| | J1.1 | $2 \times 10^2$ |
| | J13R | $11 \times 10^7$ |
| HSV-1(F) | J1.1 | $6 \times 10^3$ |
| | J13R | $4 \times 10^3$ |

*cell lines derived from human brain tumors.

**The cells were exposed to 0.01 PFU of R5111 or HSV-1(F) per cell and harvested 24 hours after infection. Progeny virus were titered on Vero cells.

This disclosure contains an exemplary description of the construction and properties of a recombinant HSV virus, R5111. In R5111, the heparan sulfate binding sites on the surface of the viral particle were ablated to preclude or at least reduce the attachment of virus to non-targeted cells. Attachment even in the absence of fusogenic activity may lead to endocytosis, degradation of the virus particle, and to potential damage to the cell by lysosomal enzymes (Zhou et al. 2002; Zhou et al. 2000). At the same time, a copy of IL13 was inserted into gC to enhance binding of virus particles to the IL13Rα2 receptor. The major restructuring of the viral genome consisted of insertion of IL13 at amino acid 24 of gD. Available data indicate that this modification ablates the gD binding site for the HveA receptor (Carfi et al. 2001). The data obtained using R5111 indicate that the virus retains the capacity to interact with the nectin receptor. Nonetheless, the R5111 targeted HSV was able to infect and replicate in J13R cells but not in the parental, J1.1 cells.

REFERENCES

Davis F G, Freels S, Grutsch J, Barlas S, Brem S. (1998) *J. Neurosurg.* 88:1-10.

Pyles R B, Warnick R E, Chalk C L, Szanti B E, Parysek L M. (1997) *Hum Gene Ther.* 8(5):533-44.

Rampling R, Cruickshank G, Papanastassiou V, Nicoll J, Hadley D, Brennan D, Petty R, MacLean A, Harland J, McKie E, Mabbs R, Brown M. (2000) *Gene Ther.* 7(10):859-66.

McKie E A, Brown S M, MacLean A R, Graham D I. (1998) *Neuropathol Appl Neurobiol.* 24(5):367-72.

Markert J M, Medlock M D, Rabkin S D, Gillespie G Y, Todo T, Hunter W D, Palmer C A, Feigenbaum F, Tomatore C, Tufaro F, Martuza R L. (2000) *Gene Ther.* 7(10):867-74.

Mineta T, Rabkin S D, Yazaki T, Hunter W D, Martuza R L. (1995) *Nat Med.* 1(9)-938-43.

Simard C, Langlois I, Styger D, Vogt B, Vlcek C, Chalifour A, Trudel M, Schwyer M. (1995) *Virology.* 212(2):734-40.

Chou J, Chen J J, Gross M, Roizman B. (1995) *Proc Natl Acad Sci USA.* 92(23):10516-20.

He B., Chou J, Brandimarti R, Mohr I, Gluzman Y, Roizman B. (1997) *J Virol.* 71(8):6049-54

Cassady K A, Gross M, Roizman B. (1998) *J Virol.* 72(9):7005-11.

Leib, D. A., Harrison, T. E., Laslo, K. M., Machalek, M. A., Moorman N. J. and Virgin, H. A. W. (1999) *J. Exp. Med.* 189:663-672.

Laquerre S, Argnani R, Anderson D B, Zucchini S, Manservigi R, Glorioso J C. (1998). *J Virol.* 72(7):6119-30.

Spear, P. G., R. J. Eisenberg, and G. H. Cohen. (2000) *Virology* 275:1-9.

Montgomery, R. I., M. S. Waner, B. J. Lum, and P. G. Spear. (1996) *Cell* 87:427-436.

Campadelli-Fiume, G., F. Cocchi, L. Menotti, and M. Lopez. (2000) *Reviews in Medical Virology.* 10:305-319.

Zhou G. Roizman B. (2002) *J Virol.* 76(12):6197-204.

Debinski W, Gibo D M, Hulet S W, Connor J R, Gillespie G Y. (1999) *Cancer Res.* 5:985-990.

Mintz A, Gibo D M, Slagle-Webb B, Christensen N D, Debinski W. (2002) *Neoplasia* 4:388-399.

Debinski W. (1998) *Crit. Rev. Oncogen.* 9:255-268.

Debinski W, Gibo D M. (2000) *Mol. Med.* 6:440-449.

Zhou G, Roizrnan B. (2001) *J Virol.* 75(13):6166-72.

Arsenakis M, Tomasi L F, Speziali V, Roizman B, Campadelli-Fiume G. (1986) *J Virol.* 58(2):367-76.

Ye G J, Roizman B. (2000) *Proc Natl Acad Sci USA.* 97(20):11002-7.

Zhou G, Galvan V, Campadelli-Fiume G, Roizman B. (2000) *J Virol.* 74(24):11782-91.

Carfi A, Willis S H, Whitbeck J C, Krummenacher C, Cohen G H, Eisenberg R J, Wiley D C. (2001) *Mol Cell.* 8(l):169-79.

Cocchi, F., Menotti, L., Mirandola, P and Campadelli-OFiume, G. (1998) J. Virol. 72:9992-10002.

Debinski W, Thompson J P. 1999. *Clin Cancer Res.* 5(10 Suppl):3143s-3147s.

Brooks, P. C., Clark, R. A. F., and Cheresh, D. A. Requirement of vascular integrin $\alpha_v\beta_3$ for angiogenesis. Science 264:569-571, 1994.

Brooks, P. C., Montgomery, A. M. P., Rosenfeld, M., Reisfeld, R. A., HU, T., Klier, G., and Cheresh, D. A. Integrin $\alpha_v\beta_3$ antagonists promote tumor regression by inducing apoptosis of angiogenic blood vessels. Cell 79:1157-1164, 1994.

Burger, M. J., Tebay, M. A., Keith, P. A., Samaratunga, H. M., Clements, J., Lavin, M. F., and Gardiner, R. A. Expression analysis of δ-Catenin and prostate-specific membrane antigen: Their potential as diagnostic markers for prostate cancer. Int. J. Cancer 100:228-237, 2002.

Ellerman, T. C., Domagala, T., McKem N. T. et al, Identification of the determinant of Epidermal growth factor receptor ligand-binding specificity using truncated, high affinity form of the ectodomain. 2001 Biochemistry 40 8930-8939.

Genbitsky, D. S., Bozso, Z., O'Flaharty, M. et al., 2001 A specific binding site for a fragment of the B-loop of epidermal growth factor and related peptides. Peptides 23:97-102 A.

Urbanelli, L., Ronchini, C., Fontana, L. et al., Tergeted gene transduction of mammalian cells expressing the HER2/neu receptor by filamentous phage. *J Mol Biol.* 2001 Nov 9;313 (5):965-76.

Hayashi, T., Takahashi, T., Motoya, S., et al. MUC1 Mucin core protein binds to the dfomasin of ICAM-1 2001 Digestion 63:87-92.

Fracasso, G., Bellisola, G., Cingarlini, S., Castelletti, D., Prayer-Galletti, T., Pagano, F., Tridente, G., and Colombatti, M. Anti-tumor effects of toxins targeted to the prostate specific membrane antigen. Prostate 53:9-23, 2002.

Mabjeesh, N. J., Zhong, H., and Simons, J. W. Gene therapy of prostate cancer: current and future directions. Endo. Related Cancer 9:115-139,2002.

Ross, S., Spencer, S. D., Holcomb, I., Tan, C., Hongo, J., Devaux, B., Rangell, L., Keller, G. A., Schow, P., Steeves, R. M., Lutz, R. J., Frantz, G., Hillan, K., Peale, F., Tobin, P., Eberhard, D., Rubin, M. A., Lasky, L. A., and Koeppen, H. Prostate stem cell antigen as therapy target: Tissue expression and in Vivo efficacy of an immunoconjugate. Cancer Res. 62:2546-2553, 2002.

Ruoslahti, E. RGD and other recognition sequences for integrins. Annu. Rev. Cell Dev. Biol. 12:697-715, 1996.

Thomas, J., Gupta, M., Grasso, Y., Reddy, C. A., Heston, W. D., Zippe, C., Dreicer, R., Kupelian, P. A., Brainard, J., Levin, H. S., and Klein, E. A. Preoperative combined nested reverse transcriptase polymerase chain reaction for prostate-specific antigen and prostate-specific membrane antigen does not correlate with pathologic stage or biochemical failure in patients with localized prostate cancer undergoing radical prostatectomy. *J. Clin. Oncol.* 20:3213-3218, 2002.

Lorimer and Lavictoire, Targeting retrovirus to cancer cells expressing a mutant EGF receptor by insertion of a single chain antibody variable domain in the envelope glycoprotein receptor binding lobe, *J Immunol Methods* 237(1-2):147-57, 2000.

Turner et al., Glycoproteins gB, gD, and gHgL of Herpes Simplex Virus Type 1 are Necessary and Sufficient t Medi ate membrane fusion in a Cos cell transfection system, *J of Virol,* 72(1): 873-75, 1998.

Brunetti et al., Herpes Simplex Virus gD and Virions Accumulate in Endosomes by Mannose 6-Phosphate-Dependent and -Independent Mechanisms, *J of Virol,* 72(4):3330-3339, 1998.

Sharma et al., Molecular imaging of gene expression and protein function in vivo with PET and SPECT, *J Magn Reson Imaging,* 16(4):336-51, 2002.

Vries et al., Scintgraphic Imaging of HSVtk Gene Therapy, *Curr Pharm Des,* 8(16):1435-50, 2002.

Vries et al., Positron emission tomography: measurement of transgene expression, *Methods,* 27(3):234, 2002.

Soling et al., Intracellular localization of Herpes simplex virus type 1 thymidine kinase fused to different fluorescent proteins depends on choice of fluorescent tag, *FEBS Lett,* 527(1-3):153, 2002.

The invention claimed is:

1. A method of killing a target cell, comprising contacting the target cell with a recombinant HSV particle, wherein the HSV particle comprises an altered gD forming a fusion with a peptide ligand to a receptor specific to the cell wherein the altered gD exhibits reduced binding to at least one of the cellular receptors of wild type gD.

2. The method of claim 1, wherein the recombinant herpes simplex virus (HSV) particle further comprises at least a second altered viral surface protein, wherein the alteration reduces binding of the second viral surface protein to a sulfated proteoglycan.

3. The method of claim 2, wherein the second altered viral surface protein is selected from the group consisting of gB and gC.

4. The method of claim 1, wherein the altered gD exhibits reduced binding to HveA or HveC.

5. The method of claim 1, wherein the recombinant HSV comprises a second fusion protein comprising a ligand fused with a viral surface protein selected from the group consisting of gB and gC.

6. The method of claim 1, wherein the ligand binds a receptor on the surface of a cell.

7. The method of claim 1, wherein the target cell is a cancer cell.

8. The method of claim 7, wherein the cancer cell is a tumor cell.

9. The method of claim 7, wherein the cancer cell is a malignant gliomal cell.

10. The method of claim 1, wherein the ligand is a cytokine.

11. The method of claim 10, wherein the cytokine is IL13.

12. The method of claim 1, wherein the ligand is a single-chain antibody.

13. The method of claim 5, wherein the second fusion protein comprises a ligand fused with gC.

* * * * *

SEQUENCE LISTING

```
<160> NUMBER OF SEQ ID NOS: 24

<210> SEQ ID NO 1
<211> LENGTH: 60
<212> TYPE: DNA
<213> ORGANISM: Artificial sequence
<220> FEATURE:
<223> OTHER INFORMATION: Synthetic primer

<400> SEQUENCE: 1

cattgctctc acttgccttg gcggctttgc ctccccaggc cctgtgcctc cctctacagc      60


<210> SEQ ID NO 2
<211> LENGTH: 60
<212> TYPE: DNA
<213> ORGANISM: Artificial sequence
<220> FEATURE:
<223> OTHER INFORMATION: Synthetic primer

<400> SEQUENCE: 2

gcagctagcc tcatggcgct tttgttgacc acggtcattg ctctcacttg ccttggcggc      60


<210> SEQ ID NO 3
<211> LENGTH: 30
<212> TYPE: DNA
<213> ORGANISM: Artificial sequence
<220> FEATURE:
<223> OTHER INFORMATION: Synthetic primer

<400> SEQUENCE: 3

gagctcggat cctgaattca accgtccctc                                        30


<210> SEQ ID NO 4
<211> LENGTH: 28
<212> TYPE: DNA
<213> ORGANISM: Artificial sequence
<220> FEATURE:
<223> OTHER INFORMATION: Synthetic primer

<400> SEQUENCE: 4

gacacgggct accctcacta tcgagggc                                          28


<210> SEQ ID NO 5
<211> LENGTH: 30
<212> TYPE: DNA
<213> ORGANISM: Artificial sequence
<220> FEATURE:
<223> OTHER INFORMATION: Synthetic primer

<400> SEQUENCE: 5

ggtgatgttc gtcaggacct cctctaggtc                                        30


<210> SEQ ID NO 6
<211> LENGTH: 26
```

-continued

<212> TYPE: DNA
<213> ORGANISM: Artificial sequence
<220> FEATURE:
<223> OTHER INFORMATION: Synthetic primer

<400> SEQUENCE: 6
gttcttcttc ggtttcggat cccccg 26

<210> SEQ ID NO 7
<211> LENGTH: 26
<212> TYPE: DNA
<213> ORGANISM: Artificial sequence
<220> FEATURE:
<223> OTHER INFORMATION: Synthetic primer

<400> SEQUENCE: 7
cggcatttcc ggaataacgc ccactc 26

<210> SEQ ID NO 8
<211> LENGTH: 27
<212> TYPE: DNA
<213> ORGANISM: Artificial sequence
<220> FEATURE:
<223> OTHER INFORMATION: Synthetic primer

<400> SEQUENCE: 8
cagaaaaccg gatcccccaa agccgcc 27

<210> SEQ ID NO 9
<211> LENGTH: 27
<212> TYPE: DNA
<213> ORGANISM: Artificial sequence
<220> FEATURE:
<223> OTHER INFORMATION: Synthetic primer

<400> SEQUENCE: 9
gccaacacaa actcgtcgta cgggtac 27

<210> SEQ ID NO 10
<211> LENGTH: 31
<212> TYPE: DNA
<213> ORGANISM: Artificial sequence
<220> FEATURE:
<223> OTHER INFORMATION: Synthetic primer

<400> SEQUENCE: 10
cagttatcct taaggtctct tttgtgtggt g 31

<210> SEQ ID NO 11
<211> LENGTH: 52
<212> TYPE: DNA
<213> ORGANISM: Artificial sequence
<220> FEATURE:
<223> OTHER INFORMATION: Synthetic primer

<400> SEQUENCE: 11
ccggaattcc ggagatcttc cctcgaggac cggaaggtct ttgccgcgaa ag 52

<210> SEQ ID NO 12
<211> LENGTH: 43
<212> TYPE: DNA
<213> ORGANISM: Artificial sequence
<220> FEATURE:
<223> OTHER INFORMATION: Synthetic primer

<400> SEQUENCE: 12
ccggaattcc ggggtaccct ggaccagctg accgaccctc cgg     43

<210> SEQ ID NO 13
<211> LENGTH: 32
<212> TYPE: DNA
<213> ORGANISM: Artificial sequence
<220> FEATURE:
<223> OTHER INFORMATION: Synthetic primer

<400> SEQUENCE: 13
cggggggatg cgcagcggga gggcgtactt ac     32

<210> SEQ ID NO 14
<211> LENGTH: 31
<212> TYPE: DNA
<213> ORGANISM: Artificial sequence
<220> FEATURE:
<223> OTHER INFORMATION: Synthetic primer

<400> SEQUENCE: 14
ccgctcgaga tggcgctttt gttgaccacg g     31

<210> SEQ ID NO 15
<211> LENGTH: 29
<212> TYPE: DNA
<213> ORGANISM: Artificial sequence
<220> FEATURE:
<223> OTHER INFORMATION: Synthetic primer

<400> SEQUENCE: 15
ggggtaccgt tgaaccgtcc ctcgcgaaa     29

<210> SEQ ID NO 16
<211> LENGTH: 31
<212> TYPE: DNA
<213> ORGANISM: Artificial sequence
<220> FEATURE:
<223> OTHER INFORMATION: Synthetic primer

<400> SEQUENCE: 16
ccgctcgaga tggcgctttt gttgaccacg g     31

<210> SEQ ID NO 17
<211> LENGTH: 29
<212> TYPE: DNA
<213> ORGANISM: Artificial sequence
<220> FEATURE:
<223> OTHER INFORMATION: Synthetic primer

<400> SEQUENCE: 17
ggggtaccgt tgaaccgtcc ctcgcgaaa     29

<210> SEQ ID NO 18
<211> LENGTH: 31
<212> TYPE: DNA
<213> ORGANISM: Artificial sequence
<220> FEATURE:
<223> OTHER INFORMATION: Synthetic primer

<400> SEQUENCE: 18
ccgctcgaga tggcgctttt gttgaccacg g     31

<210> SEQ ID NO 19
<211> LENGTH: 29
<212> TYPE: DNA
<213> ORGANISM: Artificial sequence -continued
<220> FEATURE:
<223> OTHER INFORMATION: Synthetic primer

<400> SEQUENCE: 19
aactgcaggt tgttcggggt ggccggggg 29

<210> SEQ ID NO 20
<211> LENGTH: 30
<212> TYPE: DNA
<213> ORGANISM: Artificial sequence
<220> FEATURE:
<223> OTHER INFORMATION: Synthetic primer

<400> SEQUENCE: 20
aagatttggg ctagcatggc tttcgtttgc 30

<210> SEQ ID NO 21
<211> LENGTH: 51
<212> TYPE: DNA
<213> ORGANISM: Artificial sequence
<220> FEATURE:
<223> OTHER INFORMATION: Synthetic primer

<400> SEQUENCE: 21
tccctcgaag cttcaagcat aatctggcac atcatatgta tcacagaaaa a 51

<210> SEQ ID NO 22
<211> LENGTH: 568
<212> TYPE: DNA
<213> ORGANISM: Herpes Simplex Virus

<400> SEQUENCE: 22
gcttggtcgg gaggccgcat cgaacgcaca cccccatccg gtggtccgtg tggaggtcgt 60
ttttcagtgc ccggtctcgc tttgccggga acgctagcct catggcgctt ttgttgacca 120
cggtcattgc tctcacttgc cttggcggct ttgcctcccc aggccctgtg cctccctcta 180
cagccctcag gtacctcatt gaggagctgg tcaacatcac ccagaaccag aaggctccgc 240
tctgcaatgg cagcatggta tggagcatca acctgacagc tggcatgtac tgtgcagccc 300
tggaatccct gatcaacgtg tcaggctgca gtgccatcga gaagacccag aggatgctga 360
gcggattctg cccgcacaag gtctcagctg ggcagttttc cagcttgcat gtccgagaca 420
ccaaaatcga ggtggcccag tttgtaaaag atctgctctt acatttaaag aaactttttc 480
gcgagggacg gttgaattcc acccgcatgg agttccgcct ccagatatgg cgttactcca 540
tgggtccgtc ccccccaatc gctccggc 568

<210> SEQ ID NO 23
<211> LENGTH: 350
<212> TYPE: DNA
<213> ORGANISM: Herpes Simplex Virus

<400> SEQUENCE: 23
gggtcctggt ggcgtcggcg gctccgagtt cccccggcac gcctggggtc gcggccgcga 60
cccaggcggc gaacgggggga cctgccactc cggcgccgcc cgcccctggc cccgccccaa 120
cgggggatcc gaaaccgaag aagaacagaa aaccgaaacc cccaaagcgc cgcgccccgc 180
cggcgacaac gcgaccgtcg ccgcgggcca cgccaccctg cgcgagcacc tgcgggacat 240
caaggcggag aacaccgatg caaactttta cgtgtgccca ccccccacgg gcgccacggt 300
ggtgcagttc gagcagccgc gccgctgccc gacccggccc gagggtcaga 350

-continued

```
<210> SEQ ID NO 24
<211> LENGTH: 655
<212> TYPE: DNA
<213> ORGANISM: Herpes Simplex Virus

<400> SEQUENCE: 24

atgggggggg ctgccgccag gttgggggcc gtgattttgt ttgtcgtcat agtcggcctc     60

catggggtcc gcggcaaata tgccttggcg gatgcctctc tcaagctggc cgaccccaat    120

cgctttcgcc gcaaagacct tccggtcctc gagatggcgc ttttgttgac cacggtcatt    180

gctctcactt gccttggcgg ctttgcctcc ccaggccctg tgcctcccct ctacagccct    240

cagggagctc attgaggagc tggtcaacat cacccagaac cagaaggctc cgctctgcaa    300

tggcagcatg gtttggagca tcaacctgac agctggcatg tactgtgcag ccctggaatc    360

cctgatcaac gtgtcaggct gcagtgccat cgagaagacc cagaggatgc tgggcggatt    420

ctgcccgcac aaggtctcag ctgggcagtt ttccagcttg catgtccgag acaccaaaat    480

cgaggtggcc cagtttgtaa aggacctgct cttacattta aagaaacttt ttcgcgaggg    540

acggttcaac tgaaacggta ccctggacca gctgaccgac cctccggggg tccggcgcgt    600

gtaccacatc caggcgggcc taccggaccc gttccagccc cccagcctcc cgatc         655
```